United States Patent

Begley et al.

Patent Number: 5,286,859
Date of Patent: Feb. 15, 1994

[54] METHOD OF FORMING A PHOTOGRAPHIC WASHOUT COUPLER (BARC) USING A STRONG BASE

[75] Inventors: William J. Begley, Webster; Donald Singleton, Jr., Hamlin, both of N.Y.

[73] Assignee: Eastman Kodak Company, Rochester, N.Y.

[21] Appl. No.: 906,245

[22] Filed: Jun. 29, 1992

[51] Int. Cl.$^5$ ............... C07D 295/155; C07C 329/06
[52] U.S. Cl. ............................. 544/140; 558/248
[58] Field of Search ............... 544/159; 558/248

[56] References Cited

U.S. PATENT DOCUMENTS

| | | | |
|---|---|---|---|
| 2,307,679 | 1/1943 | Hechenbleikner | 558/248 |
| 3,637,790 | 1/1972 | Traber et al. | 558/248 |
| 3,789,061 | 1/1974 | Hoyer et al. | 558/248 |
| 4,248,962 | 2/1981 | Lau | 430/382 |
| 4,409,323 | 10/1983 | Sato et al. | 430/544 |
| 4,482,629 | 11/1984 | Nakagawa et al. | 430/542 |
| 4,737,518 | 4/1988 | Nomura et al. | 558/248 |
| 4,861,701 | 8/1989 | Burns et al. | 430/543 |
| 4,912,024 | 3/1990 | Michno et al. | 430/544 |
| 4,959,299 | 9/1990 | Sakanoue et al. | 430/544 |
| 5,026,628 | 6/1991 | Begley et al. | 430/382 |

FOREIGN PATENT DOCUMENTS 193389  9/1986  European Pat. Off. .

*Primary Examiner*—Robert W. Ramsuer
*Attorney, Agent, or Firm*—Andrew Alexander

[57] ABSTRACT

A method of forming a photographic coupler (A) having the formula:

$$(SOL)_x-COUP-(R^1)_y-(R^2)_z-BLEACH$$

comprising:
(a) providing a coupler (B) having a coupling-off group represented by the formula:

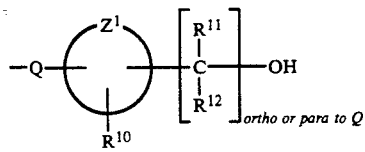

(b) reacting said coupling-off group of coupler (B) with phosgene to provide a chloroformate coupling-off group of coupler (B)
(c) reacting said chloroformate coupling-off group of coupler (B) in the presence of a strong base selected from the group consisting of triethylamine, N,N-diisopropylethylamine, and tetramethylguanine with:

$$R^{14}-R^{13}-SH$$

to provide the $R^2$ group and the BLEACH group of the coupler (A).

4 Claims, No Drawings

METHOD OF FORMING A PHOTOGRAPHIC WASHOUT COUPLER (BARC) USING A STRONG BASE

This invention relates to new photographic couplers, such as naptholic and acylanilide couplers, that are capable of forming washout dyes and releasing bleach accelerator groups in a photographic material upon photographic processing for formation of an improved image and to a photographic material and process using such compounds.

Various ways are known in the photographic art for release of a photographically useful group (PUG) from a compound, such as a photographic coupler, in a photographic material and process. For example, U.S. Pat. Nos. 4,248,962; 4,409,323 and 4,861,701 describes groups that enable timed release of a photographically useful group. Bleach accelerator groups have also been used as coupling-off groups, such as described in European Patent Specification No. 193389 and U.S. Pat. Nos. 4,861,701; 4,959,299 and 4,912,024.

The part of the compound that remains in the photographic material after release of the coupling-off groups and the dye that is formed in the material from the reaction with oxidized developer often provide undesired properties in the photographic material during or after photographic processing. For example, the dye formed from a coupler upon release of the coupling-off group often adversely affects the desired image. One answer to this problem has been to provide a water-solubilizing group on the parent coupler to enable the dye formed from the coupler to be washed out of the photographic element upon photographic processing. Such couplers are described in, for example, U.S. Pat. Nos. 4,482,629 and 5,026,628.

A class of washout couplers (couplers capable of forming dyes that may be washed out of photographic materials containing such couplers upon photographic processing) that are especially useful is the naphtholic class of couplers, such as described in U.S. Pat. Nos. 4,482,629 and 5,026,62. However, such couplers have not provided both enabling of washout of the dye formed and bleach acceleration upon processing of the photographic material containing such a coupler.

The present invention solves this problem by means of a color photographic element comprising a support bearing at least one photographic silver halide emulsion layer, an image dye-forming coupler, and a bleach accelerating releasing coupler (BARC), coupler (A), capable of forming a compound that is washed out of the photographic element upon processing; wherein, the coupler (A) is represented by the formula:

$(SOL)_x$—COUP—$(R^1)_y$—$(R^2)_z$—BLEACH wherein:
SOL is a water solubilizing group;
SOL is known in the photographic art such as described in U.S. Pat. No. 5,026,628. The water solubilizing group can be selected from such groups as carboxyl, sulfo, and hydroxyl groups which may also form a salt as described in U.S. Pat. No. 4,482,629 and is of sufficient hydrophilicity to impart good alkali solubility to the dye formed by the coupling reaction with an oxidized product of a color forming developing agent with the coupler (A). Preferred SOL groups are $-CONH_2$, $-CONHCH_3$, $-CO_2H$ and $-OH$;

COUP is a coupler moiety, such as a cyan, magenta or yellow dye forming coupler moiety;
$R^1$ is selected from a timing group and a releasing group;
$R^2$ is selected from $-OC(O)-$, $-OC(S)-$, $-SC(O)-$ and $-SC(S)-$;
BLEACH is a bleach accelerator group that is capable of being released upon processing;
x is 1, 2, or 3; and
y and z individually are 0, 1 or 2.

Such couplers enable not only the washout of dyes formed from the coupler during photographic processing but also the acceleration of bleaching of the silver formed during processing. Couplers of the invention can be coated in imaging layers, non-imaging layers or interlayers. Non-imaging layers or interlayers can contain interlayer scavengers, filter dyes of any type known in the photographic art including solid particle dispersion, conventional oil in water dispersed filter dyes and washout filter dyes, non-imaging silver emulsions such as fine particle Carey-Lea or Lippmann emulsion containing layers, or yellow colored silver emulsions which are non-imaging layers. The interlayers can be located between imaging layers, between non-imaging layers, between an imaging and an non-imaging layer, between an antihalation layer and an interlayer or between an antihalation and an imaging layer. In addition to releasing a bleach accelerator group, said couplers behave as photographic scavengers, forming washout dyes, and preventing excess oxidized color developer from diffusing to another imaging layer. Further, when coated in an imaging or non-imaging layer, these couplers can affect the development inhibition of the silver halide in not only the layer in which it is coated but also in adjacent layers thus allowing for the use of increased amounts of development inhibiting releasing compounds in photographic elements, resulting in increased sharpness. Further, one particular advantage of locating said couplers in an interlayer is to minimize any speed loss due to direct competition of oxidized color developer for said couplers over the imaging couplers.

The coupler moiety can be nay coupler moiety that enables formation of a dye during photographic processing that can be washed out of the photographic material containing such a coupler. A preferred COUP is a naphtholic coupler moiety containing a water solubilizing group attached to a group in the 2-position of the naphtholic coupler moiety. Any water solubilizing group known in the photographic art is useful. Preferred water solubilizing groups include carboxyl, sulfo, hydroxyl, sulfonamido, carbonamido, sulfamoyl, carbamoyl and salts thereof. Amide groups such as $-CONH_2$ and $CONHCH_3$ are especially useful.

A preferred coupler (A) is a naphtholic coupler comprising a water solubilizing group in the 2-position and represented by the formula:

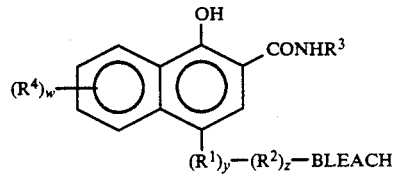

wherein:
$(R^1)_y$—$(R^2)_z$—BLEACH is a coupling-off group wherein $R^1$ is selected from a timing group and a releasing group;

$R^2$ is selected from —OC(O)—, —OC(S)—, —SC(O)— and —SC(S)—;

BLEACH is a bleach accelerator group;

y and z individually are 0, 1 or 2;

$R^4$ can be selected from hydrogen, or a substituent such as —Cl, —NO$_2$, —OCH$_3$, —NHSO$_2$R$^5$, —NHCOR$^5$, —SO$_2$NHR$^5$, —CONHR$^5$, —CO$_2$R$^5$, or —COR$^5$ and which does not adversely affect the release of (R$^1$)$_y$—(R$^2$)$_z$—BLEACH from COUP;

$R^3$ and $R^5$ is selected from the group consisting of hydrogen, substituted or unsubstituted alkyl containing 1–5 carbon atoms and substituted or unsubstituted aryl containing 6–8 carbon atoms wherein the substituted or unsubstituted alkyl or aryl is a solubilizing group or contains a solubilizing group;

at least one of $R^1$ and $R^2$ contains a photographic ballast; and w is 0, 1, 2 or 3.

A preferred $R^1$ group is selected from the group consisting of:

[chemical structure with Q, Z$^1$, R$^6$, R$^7$, R$^8$, R$^9$, N, C]

[chemical structure with —Q—, Z$^1$, R$^{10}$, R$^{11}$, R$^{12}$, ortho or para to Q]

wherein

Q is selected from O (oxygen), S (sulfur), or N (nitrogen);

$R^6$ and $R^{10}$ is hydrogen or a substituent selected from substituted or unsubstituted alkyl and substituted or unsubstituted aryl, nitro, hydrogen, amino, substituted amino, carboxylic acid, sulfonic acid, methoxy, chloro, bromo, ester groups such as —CO$_2$CH$_3$, keto groups such as —COCH$_3$, or —NHCOCH$_3$, —CONHCH$_3$, —NHSO$_2$CH$_3$, or —SO$_2$NHCH$_3$; $R^7$, $R^8$, $R^{11}$, and $R^{12}$ are selected from hydrogen, substituted or unsubstituted alkyl, and substituted or unsubstituted aryl;

$R^9$ is unsubstituted or substituted alkyl or substituted or unsubstituted aryl; $Z^1$ represents the atoms necessary to complete a 5 or 6 member aryl or heterocyclic group;

n is 0, 1 or 2; and at least one of $R^6$, $R^7$, $R^8$, $R^9$, $R^{10}$, $R^{11}$ and $R^{12}$ contains a photographic ballast.

$R^1$ groups useful in the invention are described in U.S. Pat. No. 4,886,736 incorporated herein by reference. Specific $R^1$ groups can be found at Col. 16, line 50 through Col. 21 and preferably contain a ballast.

A preferred $R^2$ group is:

$$-O-\overset{O}{\underset{\|}{C}}-$$

A further preferred coupler (A) is a naphtholic coupler selected from the group having the following formulae:

[naphthol structure with OH, CONHR$^3$, (R$^4$)$_w$, Q, Z$^1$, R$^6$, R$^7$, R$^8$, R$^9$, N—C—BLEACH]

and

[naphthol structure with OH, CONHR$^3$, (R$^4$)$_w$, Q, Z$^1$, R$^{10}$, R$^{11}$, R$^{12}$, R$^2$—BLEACH, ortho or para to Q]

wherein $R^2$ through $R^{12}$, w, n, Q, and $Z^1$ are as defined previously.

BLEACH as referred to herein can be represented by the formula:

—S—R$^{13}$—R$^{14}$ wherein:

$R^{13}$ is an unsubstituted or substituted alkylene containing 1 to 8 carbon atoms; and $R^{14}$ is a water solubilizing group.

The following are useful examples of $R^{13}$ groups:

—CH$_2$—   —CH$_2$.CH$_2$—   —CH$_2$.CH$_2$CH$_2$—

—CH$_2$—CH(CH$_3$)—CH$_2$—   —CH$_2$.CH$_2$CH$_2$.CH$_2$—

—CH$_2$—CH(C$_2$H$_5$)—CH$_2$.CH$_2$—   —CH$_2$—CH(CH$_3$)—CH$_2$.CH$_2$—

—CH(CH$_3$)—CH$_2$—   —CH$_2$.CH$_2$—O—CH$_2$CH$_2$—

The following $R^{14}$ groups are examples of useful water solubilizing groups:

—CO$_2$H   —NHSO$_2$CH$_3$   —NHCO$_2$CH$_3$

—NHCO$_2$C$_2$H$_5$   —SO$_3$H   —OH   —N(morpholino)

—SO$_2$NH$_2$   —NR$^{14a}$R$^{14b}$ wherein:

$R^{14a}$ is hydrogen or alkyl of 1 to 4 carbon atoms, $R^{14b}$ is alkyl of 1 to 4 carbon atoms and wherein at least one of $R^{14a}$ and $R^{14b}$ is alkyl and the total carbons in $R^{14a}$ and $R^{14b}$ is no more than 8. $R^{14a}$ and $R^{14b}$ together can form a ring.

Preferred couplers (A) are represented by the structures denoted as: B-1, B-5, B-6, B-7, B-8, B-9, B-10, B-11, B-12, B-18, B-19, B-20, B-21, B-22, and B-23.

The coupling off group as described can be any group or combination of groups that is releasable during photographic processing and enables release, with or without time delay, of BLEACH, a bleach accelerator group, used in the acceleration of bleaching of silver in the photographic material. Especially useful coupling-off groups are described in U.S. Pat. Nos. 4,912,024; 4,959,299 and European Patent Specification No. 193389, the disclosures of which are incorporated herein by reference.

Herein the term coupler refers to the entire compound including the coupler moiety and the coupling-off group. The term coupler moiety herein refers to that portion of the compound other than the coupling-off group.

The timing groups as described, when such a group is employed in the coupling-off group, can be any timing group or combination of timing groups known in the photographic art. Such timing groups enable tailoring of the timing of release of the bleach accelerator group at the appropriate time and place. Useful timing groups are described in, for example, U.S. Pat. Nos. 4,959,299; 4.861.701; 4,912,024; 4,409,323; and 4,248,962 and European Patent Specification No. 193389, the disclosures of which are incorporated herein by reference.

The releasing groups as described, when such a group is employed in the coupling-off group, can be any releasing group or combination of releasing groups known in the photographic art. Such releasing groups differ from the described timing groups in that the releasing groups do not provide a significant time delay in the release of a contiguous or adjacent group.

The water solubilizing group (SOL) can be any water solubilizing group known in the photographic art to enable wash-out of the dye formed in photographic processing from the compound (A). Typical water-solubilizing groups include groups terminated with an acid group, such as carboxy, sulfo or hydroxy which may also form a salt and other groups described in U.S. Pat. No. 4,482,629 (col. 4, lines 1-3) or an amide group. The compound (A) can have one or more water-solubilizing groups. The number and type of water-solubilizing groups should not be sufficient to make the compound (A) mobile in the photographic element prior to exposure and processing. The $(R^1)_y$—$(R^2)_z$—BLEACH can also contain one or more water-solubilizing groups if desired.

A typical water-solubilizing group (SOL) is carbonamido group —$CONHR_a$ wherein $R_a$ is hydrogen or an alkyl group containing 1 to 3 carbon atoms, preferably —$CONHCH_3$ or —$CONHC_2H_5$; or a group containing a water-solubilizing group, such as carboxy, sulfo or hydroxy groups, for instance, —$CONH_2CH_2CH_2OH$, —$CONH_2CH_2CO_2H$, or —$CONH_2CH_2CH_2CO_2H$. Such a group can be, for example, in the 2-position of the naphtholic coupler.

During photographic processing, the reaction of coupler (A) with oxidized color developing agent cleaves the bond between the coupling-off group and the coupler moiety of the coupler (A). Tailoring of the particular parts of the releasing groups and timing groups as required for a given releasable bleach accelerator group allows control over the timing and rate of the release of the bleach accelerator group.

The releasing group and/or timing groups can contain a ballast group, BALLAST, if desired. As used herein BALLAST is a ballast group that is known in the photographic art. The ballast group as described is an organic group of such size and configuration as to confer on the molecule sufficient bulk to render the molecule substantially non-diffusible from the layer in which it is coated in a photographic element. Representative ballast groups include substituted or unsubstituted alkyl or aryl groups typically containing 8 to 40 carbon atoms.

A process of forming an image having the described advantages comprises developing an exposed photographic element by means of a color developing agent in the presence of described coupler (A).

The naphtholic coupler moiety can be ballasted or unballasted provided that the dye formed upon oxidative coupling is capable of being washed out of the photographic element. It can be monomeric, or it can be part of a dimeric, oligomeric or polymeric coupler, in which case more than one group containing the bleach accelerator group can be contained in the coupler, or it can form part of a bis compound in which the bleach accelerator group forms part of a link between two coupler moieties.

The photographic element can comprise other couplers known in the photographic art. The photographic element can, for example comprise at least one photographic coupler that is capable of release during photographic processing a reagent or a photographic dye. A photographic reagent herein is a moiety that upon release further reacts with components in the photographic element, such as a development inhibitor, a development accelerator, a bleach inhibitor, a bleach accelerator, a coupler (for example, a competing coupler, a dye-forming coupler, or a development inhibitor releasing coupler (DIR coupler), a dye precursor, a dye, a developing agent (for example, a competing developing agent, a dye-forming developing agent, or a silver halide developing agent), a silver complexing agent, a fixing agent, an image toner, a stabilizer, a hardener, a tanning agent, a fogging agent, an ultraviolet radiation absorber, an antifoggant, a nucleator, a chemical or spectral sensitizer or desensitizer.

The bleach accelerator group can be present in the coupling-off group as a preformed species or it can be present in a blocked form or as a precursor. The bleach accelerator group can be for example a preformed bleach accelerator group or the bleach accelerator function can be blocked.

There follows a listing of patents and publications that describe representative couplers useful in the a photographic material of the invention:

I. Couplers

A. Couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999 and "Farbkuppler-eine Literaturubersicht," published in Agfa Mitteilungen, Band III, pp. 156-175 (1961).

Preferably such couplers are phenols and naphthols which form cyan dyes on reaction with oxidized color developing agent.

B. Couplers which form magenta dyes upon reaction with oxidized color developing agent are publications as: U.S. Pat. Nos. 2,600,788; 2,369,489; 2,343,703; 2,311,082; 3,152,896; 3,519,429; 3,062,653; 2,908,573 and "Farbkuppler-eine Mitteilungen, Band III, pp. 126-156 (1961).

Preferably such magenta dye-forming couplers are pyrazolones or pyrazolotriazole couplers.

C. Couplers which form yellow dyes upon reaction with oxidized and color developing agent are described in such representative patents and publications as: U.S. Pat. Nos. 2,875,057; 2,407,210; 3,265,506; 2,298,443; 3,048,194; 3,447,928 and "Farbkuppler-eine Mitteilungen, Band III, pp. 112-126 (1961).

Preferably such yellow dye-forming couplers are acylacetamides, such as benzoylacetamides and pivaloylacetamides.

D. Couplers which form colorless products upon reaction with oxidized color developing agent are described in such representative patents as: U.K. Patent No. 861,138; U.S. Pat. Nos. 3,632,345; 3,928,041; 3,958,993 and 3,961,959.

The naphtholic couplers of the invention are especially useful in combination with at least one development inhibitor releasing coupler (DIR couplers) known in the photographic art.

The photographic couplers of the invention can be incorporated in photographic elements by means and processes known in the photographic art. In a photographic element prior to exposure and processing the photographic coupler should be of such size and configuration that it will not diffuse through the photographic layers.

Photographic elements of this invention can be processed by conventional techniques in which color forming couplers and color developing agents are incorporated in separate processing solutions or compositions or in the element.

Photographic elements in which the compounds of this invention are incorporated can be a simple element comprising a support and a single silver halide emulsion layer or they can be multilayer, multicolor elements. The compounds of this invention can be incorporated in at least one of the silver halide emulsion layers and/or in at least one other layer, such as an adjacent layer, where they will come into reactive association with oxidized color developing agent which has developed silver halide in the emulsion layer. The silver halide emulsion layer can contain or have associated with it, other photographic coupler compounds, such as dye-forming couplers, colored masking couplers, and/or competing couplers. These other photographic couplers can form dyes of the same or different color and hue as the photographic couplers of this invention. Additionally, the silver halide emulsion layers and other layers of the photographic element can contain addenda conventionally contained in such layers.

A typical multilayer, multicolor photographic element can comprise a support having thereon a red-sensitive silver halide emulsion unit having associated therewith a cyan dye image-providing material, a green-sensitive silver halide emulsion unit having associated therewith a magenta dye image-providing material and a blue-sensitive silver halide emulsion unit having associated therewith a yellow dye image-providing material, at least one of the silver halide emulsion units having associated there with a photographic coupler of the invention. Each silver halide emulsion unit can be composed of one or more layers and the various units and layers can be arranged in different locations with respect to one another.

The light sensitive silver halide emulsions can include coarse, regular or fine grain silver halide crystals or mixtures thereof and can be comprised of such silver halides as silver chloride, silver bromide, silver bromoiodide, silver chlorobromide, silver chloroiodide, silver chlorobromoiodide and mixtures thereof. The emulsions can be negative-working or direct-positive emulsions. They can form, latent images predominantly on the surface of the silver halide grains or predominantly on the interior of the silver halide grains. They can be chemically and spectrally sensitized. The emulsions typically will be gelatin emulsions although other hydrophilic colloids are useful. Tabular grain light sensitive silver halides are particularly useful such as described in *Research Disclosure*, January, 1983, Item No. 22534, and U.S. Pat. No. 4,434,226.

The support can be any support used with photographic elements. Typical supports include cellulose nitrate film, cellulose acetate film, polyvinylacetal film, polyethylene terephthalate film, polycarbonate film and related films or resinous materials as well as glass, paper, metal and the like. Typically, a flexible support is employed, such as a polymeric film or paper support. Paper supports can be acetylated or coated with baryta and/or an a-olefin polymer, particularly a polymer of an a-olefin containing 2 to 10 carbon atoms such as polyethylene, polypropylene, ethylene-butene copolymers and the like.

The coupler (A) can be used in photographic elements in the same way as photographic couplers which release bleach accelerator groups have previously been used in photographic elements.

Depending upon the nature of the particular PUG, the couplers can be incorporated in a photographic element for different purposes and in different locations.

In the following discussion of suitable materials for use in the emulsions and elements of this invention, reference will be made to *Research Disclosure*, December, 1978, Item 17643, published by Industrial Opportunities Ltd., Homewell Havant, Hampshire, PO9 1EF, U.K., the disclosures of which are incorporated herein by reference. This publication will be identified hereafter by the term "Research Disclosure".

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents useful in the invention are p-phenylene diamines. Especially preferred are 4-amino-N,N-diethylaniline hydrochloride; 4-amino-3-methyl-N,N-diethylaniline hydrochloride; 4-amino-3-methyl-N-ethyl-N-$\beta$-(methanesulfonamido)ethylaniline sulfate hydrate; 4-amino-3-methyl-N-ethyl-N-$\beta$-hydroxyethylaniline sulfate; 4-amino-3-$\beta$-(methanesulfonamido)-ethyl-N,N-diethlaniline hydrochloride; and 4-amino-N-ethyl-N-(2-methoxyethyl)-m-toluidine di-p-toluenesulfonic acid.

The described photographic materials and processes can be used with photographic silver halide emulsions and addenda known to be useful in the photographic art, as described in, for example, Research Disclosure, December, 1989, Item No. 308,119, the disclosures of which are incorporated herein by reference With negative working silver halide the processing step described above gives a negative image. To obtain a positive (or reversal) image, this step can be preceded by development with a non-chromogenic developing agent to develop exposed silver halide, but not form a dye, and then uniformly fogging the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Compounds as described can be prepared (See route B) by providing a coupler (B) having a coupling-off group represented by the formula:

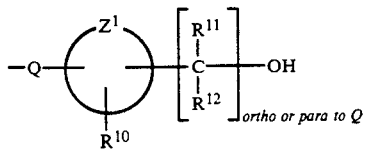

wherein

Q is selected from O (oxygen), S (sulfur), or N (nitrogen);

$R^{10}$ is hydrogen or a substituent selected from substituted or unsubstituted alkyl and substituted or unsubstituted aryl, nitro, hydrogen, amino, substituted amino, carboxylic acid, sulfonic acid, methoxy, chloro, bromo, ester as $-CO_2CH_3$ ester groups, $-COCH_3$ keto groups, and $-NHCOCH_3$, $-CONHCH_3$, $-NHSO_2CH_3$, and $-SO_2NHCH_3$;

$R^{11}$, and $R^{12}$ are selected from hydrogen, substituted or unsubstituted alkyl, and substituted or unsubstituted aryl; $Z^1$ represents the atoms necessary to complete a 5 or 6 member aryl or heterocyclic group;

at least one of COUP, $R^{10}$, $R^{11}$ and $R^{12}$ contains a photographic ballast.

The coupling-off group of coupler (B) is reacted with phosgene to provide a chloroformate coupling-off group of coupler (B) having the formula:

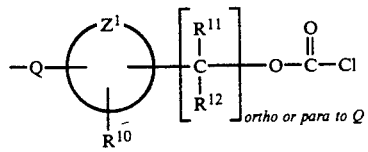

The chloroformate coupling-off group of coupler (B) is reacted in the presence of a strong base selected from the group consisting of triethylamine, N,N-diisopropylethylamine, and tetramethylguanine with:

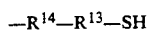

wherein:

$R^{13}$ is an unsubstituted or substituted alkylene containing 1 to 8 carbon atoms; and $R^{14}$ is a water solubilizing group.

The reaction provides the $R^2$ group and the BLEACH group of said coupler (A).

Photographic coupler (A) is a coupler capable of forming a dye which can washout of a photographic element and having a photographic ballast on at least one of $R^1$ or $R^2$, or is a coupler having a photographic ballast on the COUP rendering the coupler non-washout.

The following description illustrates these syntheses:

General Synthesis—Routes A and B

Compounds of the invention can be prepared by two routes, A and B as follows:

In route A, Scheme 1, the BLEACH G-1, is reacted with phosgene to form the thiochloroformate G-2 which is then reacted with the alcohol group of coupler G-3, in the presence of a weak base to give compounds of the invention, G-4. If G-4 contains an ester group on $R^{14}$, or another blocked solubilizing group, an additional final step is necessary to form the free solubilizing group. Examples of the synthesis of compounds of the invention using route A are given for B-1, B-7 and B-8.

In route B, Scheme 2, the alcohol group of coupler G-3 is reacted with phosgene to form the chloroformate G-5, which in the presence of a strong base is reacted with the BLEACH to give compounds G-4, of the invention. As before, if the solubilizing group $R^{14}$ was blocked during the synthesis, a final step would remove this blocking group. Examples of the synthesis of compounds of the invention using route B are given for B-1, B-5, B-6, B-7 and B-8.

Scheme 1: General Synthesis - Route A

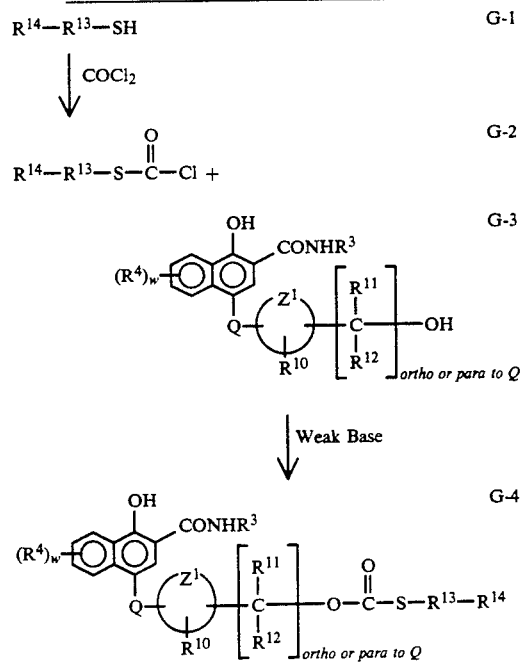

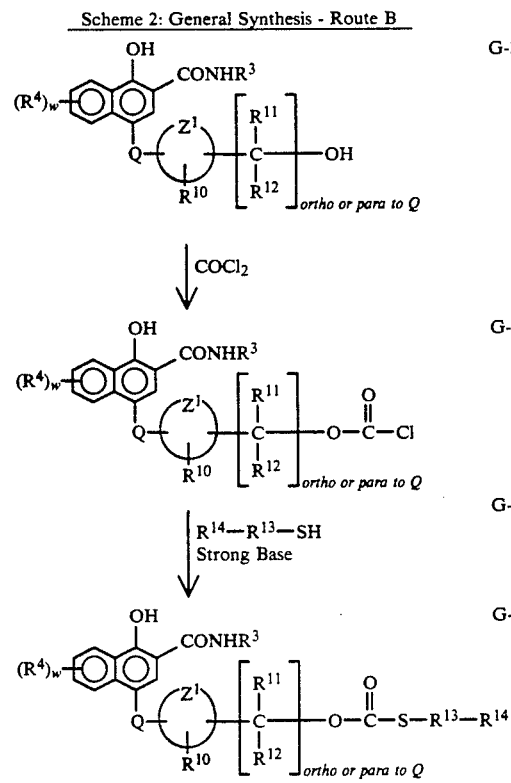

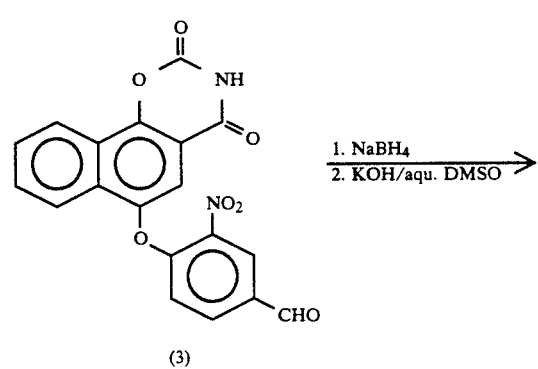

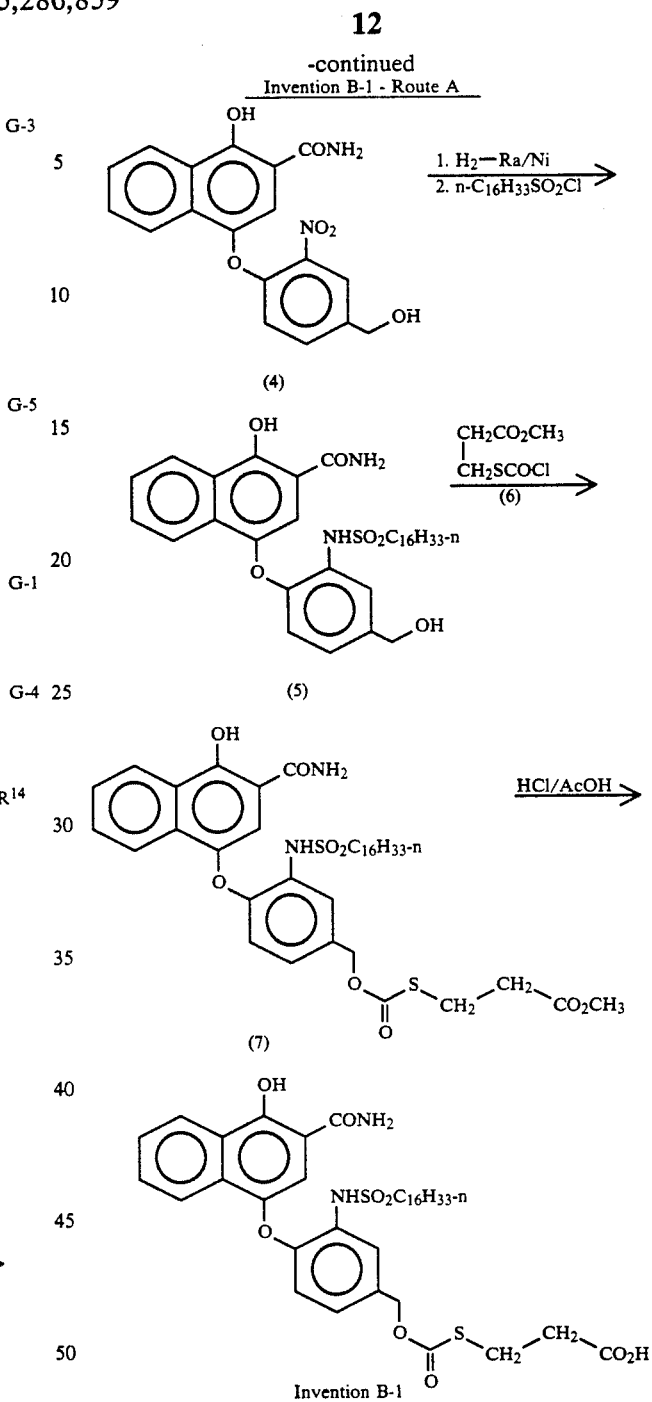

SYNTHESIS OF INVENTION COMPOUND B-1 - ROUTE A

Compound 1

Phenyl-1,4-dihydroxy-2-naphthoate, (100 g, 356.78 mMol) was dissolved in deoxygenated tetrahydrofuran, (500 mL) and deoxygenated methanol, (500 mL) added. To this solution, stirred at room temperature under a nitrogen atmosphere, was added ammonium acetate, (50.0 g, 648.63 mMol) followed by concentrated ammonium hydroxide, (1.0 L). After stirring for 3 hr. the reaction solution was then poured into ice-cold 2N-HCl, (4.0 L) and enough concentrated HCl added to bring the pH to 1. The resulting product, Compound (1), was filtered off, washed well with water and air-dried. The crude product was washed with dichloromethane and air-dried again. Yield: 62.0 g (72%).

Compound (2)

Compound (1), (50.0 g, 0.246 Mol) was dissolved in dry pyridine, (150 mL) and acetonitrile (75 mL) added. The solution was stirred and cooled to −5° to 0° C. Ethyl chloroformate, (50 mL, 0.523 Mol) was then added dropwise with stirring while maintaining the temperature at 0° C. After the addition, the cooling bath was removed and the temperature allowed to reach room temperature. The reaction mixture was then gradually heated to reflux and the solvent allowed to distill off. This procedure was continued until the temperature had risen to approximately 120° C. and 150 mL of solvent had been collected. Heating under reflux was continued for an additional 1 hr period. The reaction mixture was then cooled to approximately 50° C. and poured into 2N-HCl, (3.0 L) held at room temperature. This suspension was then stirred for approximately 15 min. filtered, and the residue washed well with water, acetonitrile, and finally ether. This gave the product, Compound (2), sufficiently pure for the next step. Yield: 43.5 g (77%).

Compound (3)

Compound (2), (23.0 g, 100.35 mMol) was taken up in deoxygenated dimethyl sulfoxide, (250 mL) and deoxygenated water, (25 mL) added. To this solution, stirred at room temperature under nitrogen, was added 85% potassium hydroxide, (9.9 g, 150.53 mMol) and stirring continued until dissolution, approximately 15 min. Then 4-chloro-3-nitrobenzaldehyde, (18.62 g, 100.35 mMol) was added all at once and the resulting solution stirred at 60° C. for 1 hr. The reaction mixture was then poured into ice-cold 2N-HCl, (2.0 L) and filtered off. The product, Compound (3), was washed with water and, while still wet, slurried in methanol, filtered and washed with ether. This product was pure enough to be used in the next step. Yield: 28.0 g (74%)

Compound (4)

Compound (3), (28.0 g, 74.01 mMol) in a powdered form was suspended in tetrahydrofuran, (150 mL) and methanol, (100 mL). Water, (100 mL) was added, followed by sodium borohydride, (2.8 g, 74.01 mMol) in small portions. More tetrahydrofuran, (50 mL) was added to aid stirring. At the end of the sodium borohydride addition, complete dissolution had been achieved. The reaction was allowed to proceed for a further 15 min. then poured into ice-cold 2N-HCl, (2.0 L) and the product filtered off. The product was washed with methanol and, while still wet, with solvent, suspended in ethanol and heated to reflux. The solution was cooled, filtered, washed with methanol, ether and finally air-dried. A second crop of material was obtained on concentrating the mother liquor. Total yield of the hydroxymethyl derivative of compound (3), 19.5 g (67%). The hydroxymethyl derivative of compound (3), (19.0 g, 50 mMol) was suspended in water, (200 mL) containing 85% potassium hydroxide, (26.34 g, 400 mMol). To this mixture was added methanol, (50 mL), and this was heated to 80° C. for 1 hr. The resulting dark yellow-brown solution was cooled and poured into ice-cold 2N-HCl, (2.0L). The yellow product, compound (4), was filtered off, washed well with water and air-dried. Yield: 17.7 g (100%).

Compound (5)

Compound (4), (17.7 g, 50 mMol) was dissolved in tetrahydrofuran, (80 mL) and methanol, (300 mL) added. Raney-Nickel which had been washed several times with water and then methanol was added and the solution hydrogenated at 55 psi for 2 hr. After this period hydrogen uptake had ceased. The catalyst was filtered off, washed with methanol, and the filtrate concentrated under reduced pressure to give the product, the amino derivative of compound (4). This product was deemed sufficiently pure to be carried on to the next step. Yield: 100%). The amino derivative of compound (4), (50.0 mMol) was dissolved in dry pyridine, (150 mL) and hexadecylsulfonyl chloride, (16.2 g, 50.0 mMol) was added. The solution was stirred at room temperature under a nitrogen atmosphere for 30 min. The pyridine was concentrated under reduced pressure and the residue taken up in ethyl acetate. This ethyl acetate solution was then washed with 2N-HCl (X3), dried (MgSO4), filtered and concentrated. The resultant residue crystallized from acetonitrile After filtering, washing with acetonitrile and drying, the yield of product, compound (5), amounted to 16.3 g, (53% calculated from compound (4)).

Methyl 3-(chlorocarbonyl)thiol]propionate (6)

Methyl 3-thiopropionate, (11.5 mL, 0.104 mMol) was dissolved in tetrahydrofuran, (100 mL) and the solution cooled to 0° C. A 20%- solution of phosgene in toluene, (205 mL, 0.415 Mol) was added in a steady stream, whereupon the temperature rose to approximately 10° C. After the phosgene had been added the cooling bath was removed and the reaction stirred for 8 hrs. and let warm to room temperature. At the end of this period the solvent and excess phosgene were removed under reduced pressure and the residual viscous liquid coevaporated with dichloromethane, (X3). The product, methyl 3[(chlorocarbonyl)thiol]propionate, (6) so obtained was used directly in the next step.

Compound (7)

Compound (5), (36.4 g, 59.3 mMol) was dissolved in tetrahydrofuran, (200 mL) and methyl 3[(chlorocarbonyl)thio]propionate, (6), (19.0 g, 103.8 mMol) in tetrahydrofuran, (30 mL) added slowly over a period of approximately 15 mins.. When all of the 3[(chlorocarbonyl)thio]propionate had been added, pyridine, (14.4 mL, 178.0 mMol) was added in a steady stream. The resulting reaction mixture was stirred at room temperature for 24 hrs. At the end of this period, the solvent from the reaction mixture was concentrated under reduced pressure and the residue taken up in ethyl acetate. The ethyl acetate solution was then washed with 2N-HCl (x3), dried (MgSO4), filtered and the solvent removed under reduced pressure. The resulting oil was dissolved in a solvent mixture of ethyl acetate/dichloromethane/heptane in the ratio 20:10:70 and pressure chromatographed using this solvent system. The first major band was collected. Yield: compound (7), 21.0 g, 47%.

Invention B-1

Compound (7), (3.0 g, 4.0 mMol) was dissolved in acetic acid, (30 mL) and concentrated hydrochloric acid, (approximately 10 mL) gradually added so that the former did not come out of solution. The reaction solution was then stirred at room temperature for 48 hrs. At the end of this period the acetic acid was removed from the reaction under reduced pressure and the residue dissolved in ethyl acetate. The ethyl acetate solution was then washed with 2.5%-$Na_2CO_3$ (x2), 2N-HCl (x1), dried ($MgSO_4$), filtered and concentrated to an oil. This oil was dissolved in a solvent mixture of ethyl acetate/heptane/acetic acid in the ratio of 40:60:1 and pressure chromatographed using the same solvent mixture. The first major band was collected to give the invention compound, (I-1). Yield: 2.0 g, 67%. Calculated for $C_{38}H_{52}N_2O_9S_2 \cdot 2CH_3COOH$: %C58.31, %H6.99, %N3.24, and %S7.41. Found: %C58.44, %H6.64, %N3.52, and %S7.79.

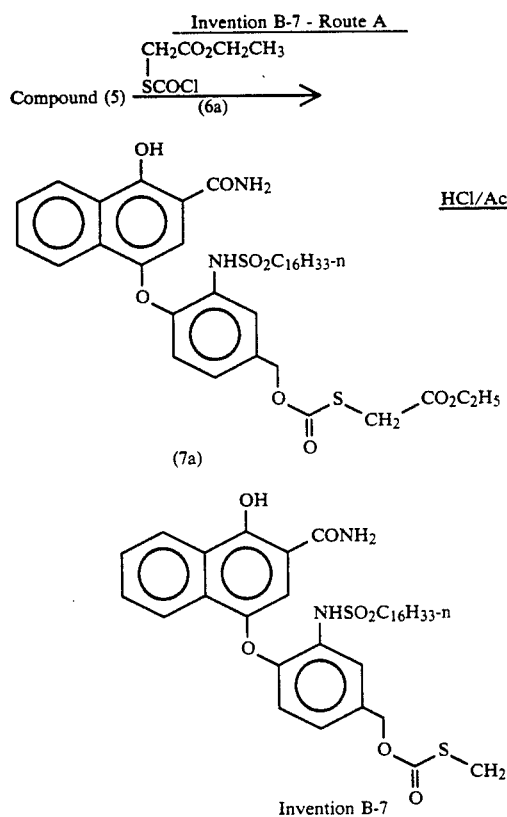

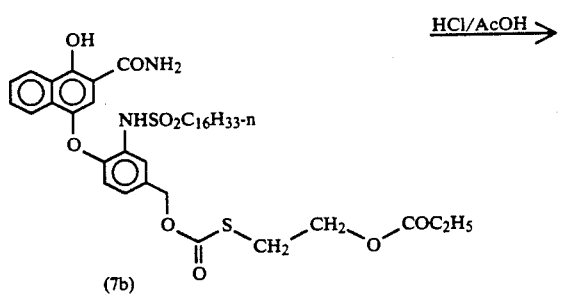

SYNTHESIS OF INVENTION COMPOUND B-7 - ROUTE A

Ethyl 2-[(chlorocarbonyl)thiol]acetate (6a)

Ethyl 2-[(chlorocarbonyl)thiol]acetate (6a), was prepared from ethyl thioacetate in a similar way to Methyl 3-[(chlorocarbonyl)thiol]propionate (6).

Compound (7a)

Compound (7a) was prepared in a similar manner to that of compound (7).

Invention B-7

Compound of the invention B-7, route A, was prepared from (7a) in a similar manner to that of invention compound B-1 from compound (7).

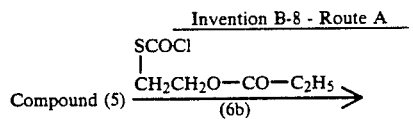

SYNTHESIS OF INVENTION COMPOUND B-8 - ROUTE A

2-[(Chlorocarbonyl)thiol]ethyl propionate (6b)

2-[(Chlorocarbonyl)thiol]propionate (6b), was prepared from 2-thioethyl propionate in a similar way to methyl 3-[(chlorocarbonyl)thiol]propionate (6).

Compound (7b)

Compound (7b) was prepared in a similar manner to that of compound (7).

Invention B-8

Compound of the invention B-8, was prepared from (7b) in a similar manner to that of invention compound B-1 from compound (7).

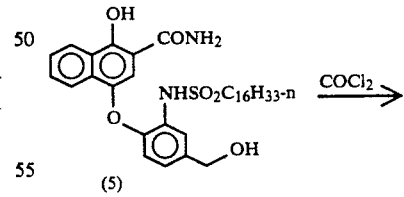

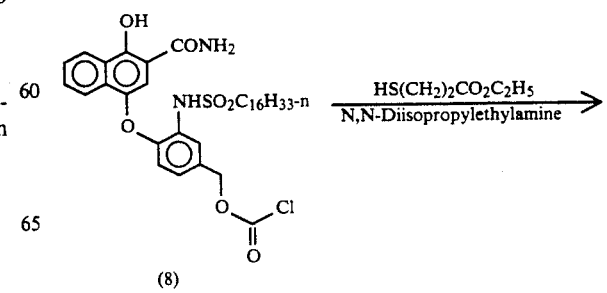

-continued
Invention B-1 - Route B

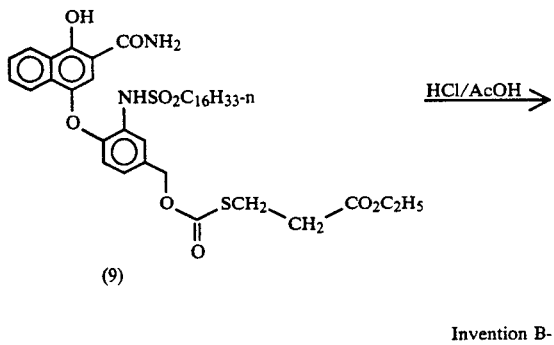

Invention B-1

SYNTHESIS OF INVENTION COMPOUND B-1 - ROUTE B

Compound (8)

Compound (5) (2.5 g, 4.08 mMol), was dissolved in tetrahydrofuran (20 mL) and treated with a solution of phosgene in toluene (5 mL of a 20% solution, 10.20 mMol). The resulting solution was stirred at room temperature for 2 hours and then concentrated under reduced pressure at room temperature. The resulting oil, without further purification was taken on to the next step.

Compound (9)

Compound (8) as described above (4.08 mMol), was dissolved in tetrahydrofuran (20 mL), to which was then added 2-thioethyl acetate (1.36 mL, 12.24 mMol) followed by N,N-diisopropylethylamine (2.1 mL, 12.24 mMol) and the resulting solution stirred at room temperature for 2 hours. At the end of this period the reaction solution was concentrated under reduced pressure, dissolved in ethyl acetate and the ethyl acetate solution washed with 2N-HCl (x3), dried (MgSO$_4$), filtered and the filtrate concentrated under reduced pressure. The residual oil, without further purification was taken on to the next step.

Invention B-1

Compound of the invention B-1, was generated from compound (9) on treating (9) with concentrated hydrochloric acid in acetic similar to the generation of B-1 from compound (7).

-continued
Invention B-5 - Route B

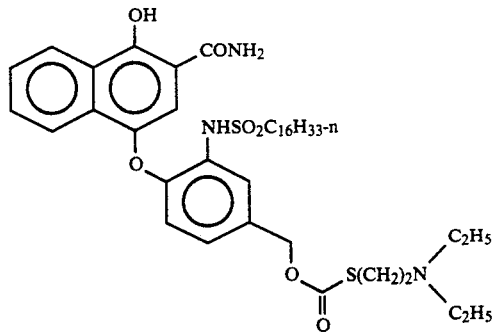

Invention B-5

SYNTHESIS OF INVENTION COMPOUND B-1 - ROUTE B

Compound (8)

Compound (5), (25.0 g, 40.8 mMol) was dissolved in tetrahydrofuran, (200 mL) and the solution cooled in an ice-bath. A 20%-solution of phosgene in toluene, (50.4 mL, 102 mMole) was added with stirring, at such a rate to keep the temperature in the range of 0°-10° C. After the addition the temperature was allowed to warm to room temperature over a 2 hr. period. After this period the reaction solution was concentrated to an oil under reduced pressure with the application of the minimum amount of heating. The residual oil was taken on to the next step.

Invention B-5

To a stirred solution of 3-diethylaminoethanethiol hydrochloride, (9.0 g, 53.0 mMole), in water, (150 mL) was added sodium carbonate, (8.6 g, 81.1 mMole). To this solution was added ethyl acetate, (200 mL) and with good stirring compound (8), (40.8 mMol) in ethyl acetate, (50 mL) was added slowly. The two phase solution was stirred at room temperature for 1 hr. At the end of this period the ethyl acetate layer was separated from the aqueous layer and the former washed with water (x1), 2N-HCl (x2), dried (MgSO$_4$), filtered and concentrated under reduced pressure. The residue was dissolved in a 35% solution of ethyl acetate in heptane and pressure chromatographed. The first major band was collected to give compound (I-2). Yield: 10 g, [(32%), calculated from compound (5)]. $C_{41}H_{61}N_3O_7S_2$: M+771. H$^1$-NMR(CDCL$_3$): δ=8.44(m, 1H, Ar), 7.78(m, 1H, Ar), 7.57(m, 3H, Ar), 7.02(s, 1H, Ar), 6.95(d, 1H, Ar), 6.57(d, 1H, Ar), 6.26(br. s, 2H, —NH$_2$), 5.12(s, 2H, benzylic —CH$_2$—), 3.24(br. t, 2H, —NHSO$_2$CH$_2$—), 2.93(m, 2H, —SCH$_2$CH$_2$N—), 2.69(m, 2H, —SCH$_2$CH$_2$N—), 2.55(q, 4H, —NCH$_2$CH$_3$), 1.90(m, 2H), 1.42(m, 2H), 1.25(s, 24H), 1.02(t, 6H, —NCH$_2$CH$_3$), 0.88(t, 3H).

Invention B-5 - Route B

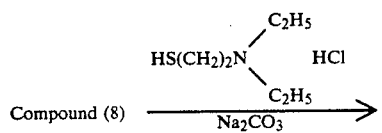

Invention B-6 - Route B

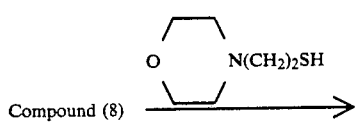

Invention B-6 - Route B

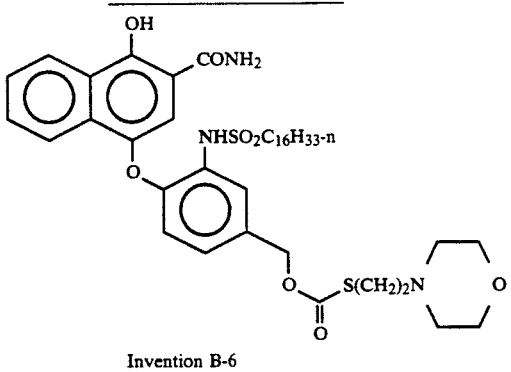

Invention B-6

SYNTHESIS OF INVENTION COMPOUND B-6 - ROUTE B.

Invention B-6

Compound (8), (40.8 mMol) was dissolved in tetrahydrofuran, (100 mL) and 3-morpholinoethanethiol, (6.6 g, 44.9 mMole) in tetrahydrofuran, (30 mL) was added at a fairly rapid rate. The resulting reaction was stirred overnight and then concentrated to an oil under reduced pressure. The residual oil was dissolved in ethyl acetate and the ethyl acetate washed with 2N-HCl (x2), dried (MgSO$_4$), filtered and concentrated to an oil. This oil was dissolved in a 30% solution of ethyl acetate in dichloromethane and pressure chromatographed using the same solvent system to remove some impurties. The product, compound (I-3), was eluted from the column on changing to a 50% solution of ethyl acetate in dichloromethane. Yield: 7.0 g, (25%). C$_{41}$H$_{59}$N$_3$O$_8$S$_2$: M+785. H$^1$-NMR(CDCL$_3$): δ=8.41(m, 1H, Ar), 7.75(m,1H, Ar), 7.59(m, 3H, Ar), 7.42(br. s, 1H, NH), 7.02(s, 1H, Ar), 6.95(d, 1H, Ar), 6.55(d, 1H, Ar), 6.4(br. s, 2H, NH$_2$), 5.12(s, 2H, benzylic —CH$_2$—), 3.59(m, 4H, —OCH$_2$CH$_2$N—), 3.25(br. t, —NHSO$_2$CH$_2$—), 2.97(t, 2H), 2.55(t, 2H), 2.41(m, 4H, —NCH$_2$CH$_2$O—), 1.92(m, 2H), 1.42(m, 2H), 1.2(s, 24 H), 0.88(t, 3H).

Invention B-7 - Route B

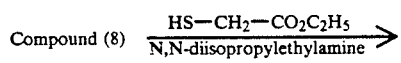

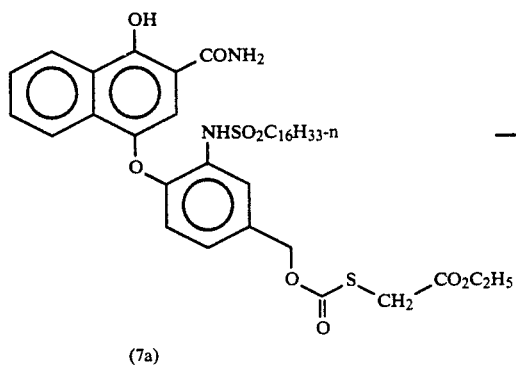

(7a)

Invention B-7

SYNTHESIS OF INVENTION COMPOUND B-7 -ROUTE B.

Compound (7a)

Compound (8) (16.3 mMol), was dissolved in tetrahydrofuran (100 mL) and ethyl thioacetate (5.36 mL, 48.9 mMol) added followed by N,N-diisopropylethylamine (8.4 mL, 48.9 mMol). The resulting solution was stirred at room temperature for 2 hours. At the end of this period the reaction solution was concentrated under reduced pressure and the residue dissolved in ethyl acetate. This ethyl acetate solution was then washed with 2N-HCl (x2), dried (MgSO$_4$), filtered and again concentrated. The residual oil was then taken on as such, to the next step.

Invention B-7

Compound of the invention B-7, route B, was prepared from (7a) in a similar manner to that of invention compound B-1 from compound (7). Yield 6.5 g, 55% based on compound (8). H$^1$-NMR(d$^6$—DMSO): δ=9.55(s, 1H, —NHSO2—), 8.50–6.55(m, 10H, Aromatics and —NH$_2$), 5.18(s, 2H, benzylic —CH$_2$—), 3.70(s, 2H, —SCH$_2$—), 3.17(br.t, 2H, —NHSO$_2$CH$_2$—), 1.72(m, 2H, —NHSO$_2$CH$_2$—CH$_2$—), 1.32–0.80(m, 29H, —NHSO$_2$CH$_2$CH$_2$C$_{14}$H$_{29}$).

Invention B-8 - Route B

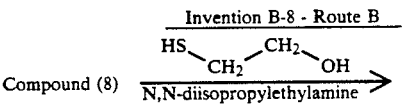

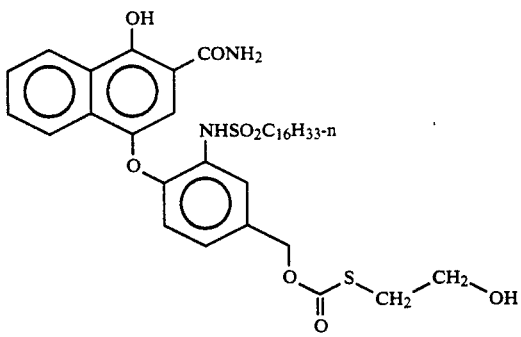

Invention B-8

SYNTHESIS OF INVENTION COMPOUND B-8 -ROUTE B

Invention B-8

Invention compound B-8 was prepared from compound (8) (8.2 mMol), 2-thioethanol (1.7 mL, 24.5 mMol) and N,N-diisopropylethylamine (4.2 mL, 24.5 mMol) in tetrahydrofuran (30 mL) in a similar manner to that described for compound (9) route B. The product was purified by pressure chromatography over silica gel with 40% ethyl acetate in heptane as solvent to give B-8 as a foam. Yield 3.5 g, 60%. The Hl-nmr and mass spectrum were identical to that of B-8 formed via route A.

The following examples and data further illustrate the invention. Photographic elements were prepared comprising the bleach accelerating releasing couplers (BARCs) forming washout dyes as described.

EXAMPLE 1

Illustrative example wherein compounds of the invention are located within an emulsion layer.

On a cellulose triacetate film support subbed with gelatin, were coated the following layers: (amounts are in grams per meter squared).

| | |
|---|---|
| Emulsion layer 1 | Gelatin - 3.2; red sensitized silver bromoiodide (as Ag) - 1.61; cyan image forming coupler C-1 - 0.75, dispersed in di-n-butylphthalate, (1:0.75, by weight); cyan dye forming DIR coupler (Development Inhibiting Releasing Coupler) DC-1 - 0.05, dispersed in N-butylacetanilide, (1:2 by weight); BARC(s), as described in Table 1, dispersed in N,N-diethyldodecanamide, (1:2 by weight); and saponin - 1.5% of melt volume. |
| Protective Overcoat | Gelatin - 5.4; bisvinylsulfonylmethyl ether - 2% of total gelatin; and saponin surfactant - 1.5% of melt volume. |

Structures of the couplers are as follows:

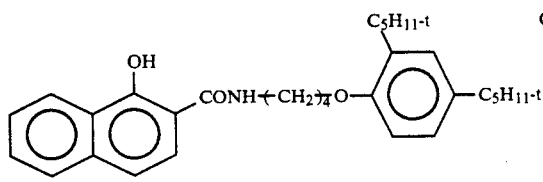

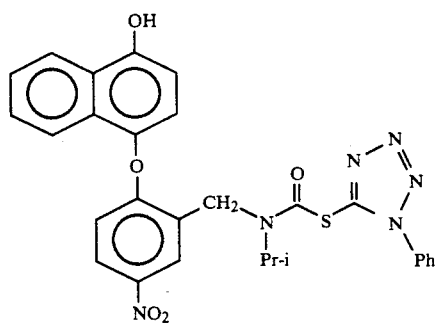

Strips of each element were exposed to red light through a graduated density step tablet and then developed 3.25 minutes at 40° C. in color developer solution CDs1, stopped, washed, bleached using bleach solutions Bls1, Bls1 modified as described, or Bls2, fixed, washed and dried. Bleach solutions referred to should not be confused with the earlier BLEACH which is a fragment released from coupler (A). The residual silver levels were measured by X-ray fluorescence.

| | |
|---|---|
| Color Developer, CDs1: | |
| Distilled Water | 800 mL |
| Sodium Metabisulfite | 2.78 g |
| Sodium Sulfite, anhydrous | 0.38 g |
| Kodak CD-4 (color developer)* | 4.52 g |
| Potassium Carbonate, anhyd. | 34.3 g |
| Potassium Bicarbonate | 2.32 g |
| Sodium Bromide | 1.31 g |
| Potassium Iodoide | 1.20 mg |
| Hydroxylamine Sulfate (HAS) | 2.41 g |
| Diethylenetriaminepentacetic acid, pentasodium salt (40% Soln.) | 8.43 g |
| Distilled Water | to 1 L |
| Adjust pH to 10.0. | |
| Bleach Solution, Bls1 | |
| Distilled water | 600 mL |
| Ammonium bromide | 150 g |
| Ammonium Ferric EDTA (1.56M, pH 7.05, 44% by weight. Contains 10% molar excess EDTA, 3.5% by weight | 175 mL |
| Glacial acetic acid | 9.5 mL |
| Sodium nitrate | 35 g |
| Distilled water | to 1 L |
| pH at 26.7° C. 6.00 +/− 0.05 Adjusted with NH$_4$OH or HNO$_3$. | |
| Bleach Solution, Bls2 | |
| Gelatin | 0.5 g |
| Sodium persulfate | 33.0 g |
| Sodium chloride | 15.0 g |
| Sodium dihydrogen phosphate (anhydrous) | 9.0 g |
| Distilled water | to 1 L |

*CD-4 is 4-amino-3-methyl-N-ethyl-N-beta-hydroxy-ethylaniline sulfate.

TABLE 1

| BARC Compound | Level$^a$ (mg/m$^2$) | % Silver Development Increase at Mid-Scale (No Bleach) | $\Delta\gamma^b$ (Using Bleach Solution Bls1) | Change in Speed ($\Delta$logE)$^c$ (Using Bleach Solution Bls1) | % Silver Remaining After 3 Mins in Modified Bleach Solution, Bls1$^d$ |
|---|---|---|---|---|---|
| Comparison Cm-1 | 31.2 | 33 | 0.25 | +0.13 | 22 |
|  | 62.4 | 50 | 0.39 | +0.17 | 19 |
| B-1 | 40.1 | 34 | 0.18 | +0.05 | 22 |
|  | 80.2 | 66 | 0.31 | +0.04 | 18 |
| B-2 | 37.7 | 28 | 0.24 | −0.03 | 28 |
|  | 75.4 | 49 | 0.36 | −0.06 | 25 |
| Comparison Cm-1 | 31.2 | 31 | 0.19 | +0.07 | 20 |
|  | 62.4 | 67 | 0.42 | +0.17 | 18 |
| B-3 | 37.0 | 16 | 0.22 | −0.06 | 24 |
|  | 74.0 | 35 | 0.30 | −0.07 | 22 |
| B-4 | 38.5 | 32 | 0.17 | +0.02 | 20 |
|  | 77.0 | 42 | 0.25 | +0.01 | 21 |
|  |  |  |  |  | Bls2 |
| Comparison | 33.4 | 14 | 0.14 | −0.02 | 71 |

TABLE 1-continued

| BARC Compound | Level[a] (mg/m$^2$) | % Silver Development Increase at Mid-Scale (No Bleach) | Δγ[b] (Using Bleach Solution Bls1) | Change in Speed (ΔlogE)[c] (Using Bleach Solution Bls1) | % Silver Remaining After 3 Mins in Modified Bleach Solution[d] |
|---|---|---|---|---|---|
| Cm-2 | 66.8 | 19 | 0.27 | −0.06 | 29 |
| B-5 | 41.5 | 76 | 0.66 | −0.12 | 20 |
|  | 83.0 | 63 | 0.59 | −0.09 | 2 |
| B-6 | 42.3 | 47 | 0.39 | −0.09 | 25 |
|  | 84.6 | 45 | 0.31 | −0.04 | 5 |

[a]These numbers represent two coating levels, 53.8 and 107.6 μMole/m$^2$.
[b]Change in contrast relative to analogous coating containing no Barc.
[c]Speed relative to analogous coating containing no Barc.
[d]Bleach solution Bls1 to which 30.0 g/L of potassium bromide was added, the resulting solution diluted 1:1 with water;

and % Silver Remaining at $D_{max} = \frac{(mg/m^2 \text{ at } t = 3 \text{ min}) \times 100}{(mg/m^2 \text{ at } t = 0 \text{ min})}$ Structures of the couplers are as follows:

Comparison Cm-1

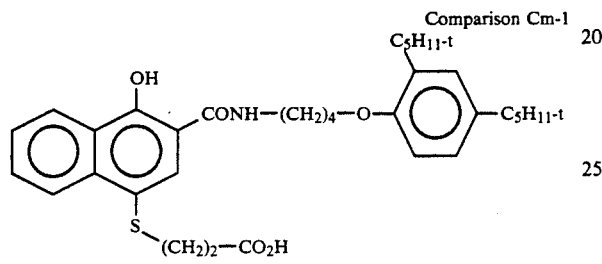

Comparison Cm-2

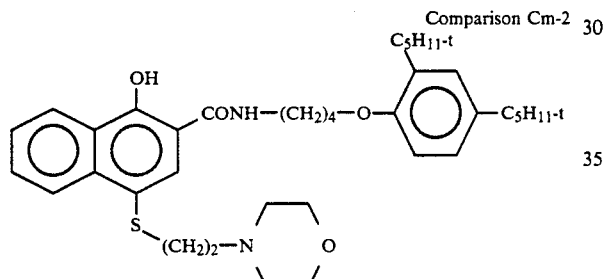

Compounds Of The Invention

B-1

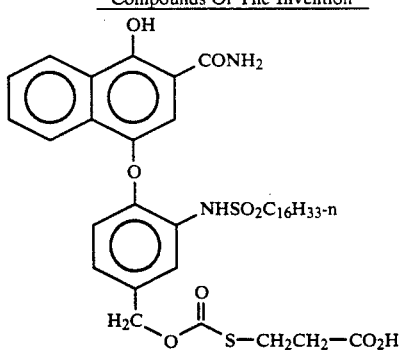

B-2

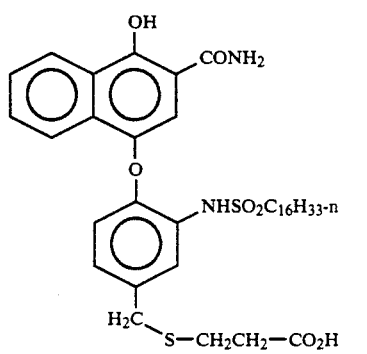

B-3

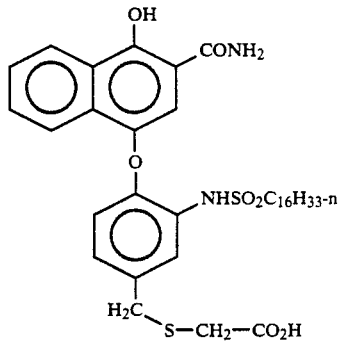

B-4

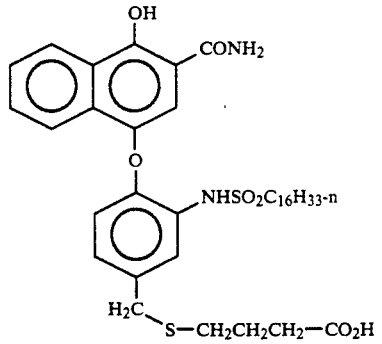

B-5

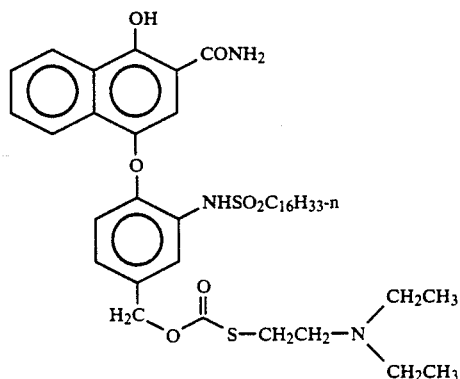

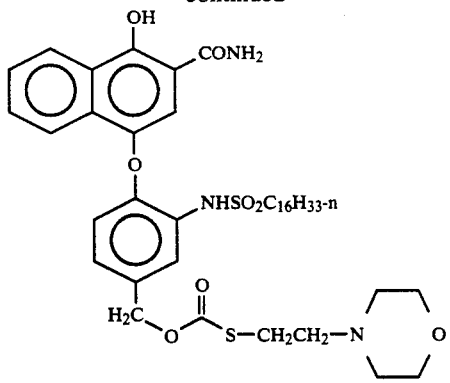

B-6

In Example 1, table 1, it can be seen that compounds of the invention B-1 and B-2, release a bleaching fragment which gives desired bleaching and contrast increases without undesired large speed increases observed with comparison compound Cm-1. The large speed increase associated with Cm-1 is due to the formation of cyan dye which does not wash out of the element.

Table 1 also shows two variations in bleaching fragment both of which contain a carboxylic acid group, released from B-3 and B-4. Both give the desired increases in contrast and bleaching performance similar to B-1 and B-2. They do not show the large speed increases associated with the comparison compound Cm-1.

Finally, Table 1 shows two variations in bleaching fragment containing different amine groups and released from B-5 and B-6. In bleaching solutions based on persulfate as described in Bls2, amine containing bleaching fragments are more effective at promoting bleaching than carboxylic acid containing bleaching fragments. B-5 and B-6 provide effective contrast increases and bleaching performance without the disadvantages associated with the non-washout nature of the dye formed from Cm-2.

EXAMPLE 2

Illustrative example wherein compounds of the invention are located in an interlayer, (between imaging layers).

On a cellulose triacetate film support subbed with gelatin, were coated the following layers: (amounts are in grams per meter squared, unless noted).

| Antihalation layer | Gelatin - 2.44; and grey collodal silver - 0.32. |
| --- | --- |
| Interlayer B | Gelatin - 0.65; and S-1 - 0.108 Mol/m² or BARC(s) - 0.108 Mole/m², as described in Table 2, dispersed in N,N-diethyldodecanamide, (1:2). |
| Emulsion layer 1: (Green Record) | Gelatin - 2.15; green sensitized silver bromoiodide (as Ag) - 1.07; magenta image forming coupler M-1 - 0.32, dispersed in dibutylphthalate, (1:½); and magenta dye forming DIR coupler (Development Inhibiting Releasing Coupler) DM-1 - 0.02, dispersed in dibutylphthalate, (1:2). |
| Interlayer A | Gelatin - 0.65; and S-1 - 0.108 Mol/m² or BARC(s) - 0.108 Mole/m², as described in Table 2, dispersed in N,N-diethyldodecanamide, (1:2). |
| Emulsion layer 2 (Blue Record) | Gelatin - 2.42; blue sensitized silver bromoiodide (as Ag) - 0.91; yellow image forming coupler Y-1 - 0.75, dispersed in dibutylphthalate, (1:½); and yellow dye forming DIAR coupler (Development Inhibiting Releasing Coupler) DY-1 - 0.05, dispersed in dibutylphthalate, (1:½). |
| Overcoat | Gelatin -.2.7; and bisvinylsulfonylmethyl ether - 1.75% total gelatin. |

Structures of the couplers, not already described in Example 1, are as follows:

-continued

DY-1

Strips of each element were exposed to white light through a graduated density step tablet and then developed 3.25 minutes at 40° C. in the color developer solution CDs1, described, stopped, washed, bleached using bleach solutions Bls2, Bls3, and modified bleach solutions Bls1 and Bls3 as described, fixed, washed and dried.

| Bleach Solution, Bls3 | |
|---|---|
| Distilled water | 600 mL |
| Ammonium bromide | 50.0 g |
| 1,3-Propanediaminetetraacetic acid | 30.27 g |
| Ammonium hydroxide (28% ammonia) | 35.20 g |
| Ferric nitrate nonahydrate | 36.40 g |
| Glacial acetic acid | 26.50 g |
| 1,3-Diamino-2-propanoltetraacetic acid (Rexpronol Acid, Grace) | 1.0 g |
| Ammonmium ferric EDTA (1.56M, pH 7.05, 44% wgt.) (contains 10% molar excess EDTA, 3.5% wgt.) | 149.0 g |
| Distilled water to make | 1.0 L |
| pH at 26.7° C. 5.25 +/− 0.10 | |
| Adjusted pH with NH$_4$OH or HNO$_3$. | |

Cm-1, showing that during processing, the dyes formed from the compounds of the invention, are washing out of the photographic elements. This in not the case for Cm-1.

Table 2 also shows that photographic elements containing compounds of the invention have lower $D_{min}$ values than those containing S-1. This shows that compounds of the invention are very effective scavengers of oxidized color developer.

Changes in speed and contrast were generally less with compounds of the invention or comparison compounds when they were coated in interlayers, see Table 1, compared with emulsion containing layers.

Compounds of the invention give excellent bleaching when coated in interlayers.

Other compounds of the invention are as follows:

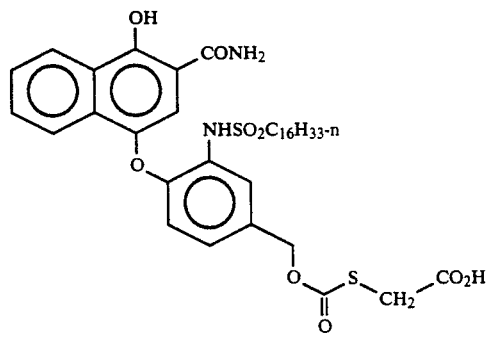

B-7

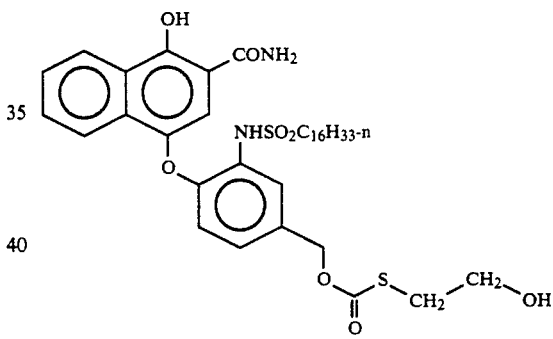

B-8

TABLE 2

| BARC Cpd. | Loc[c] | Blue Record (Using Bleach Solution Bls3) | | | Green Record (Using Bleach Solution Bls3 | | | RD[f] | % Silver Remaining[a] (3 Mins. In Bleach Soln[b]) | | |
|---|---|---|---|---|---|---|---|---|---|---|---|
| | | $D_{min}$ | $\Delta\gamma^d$ | $(\Delta\log E)^e$ | $D_{min}$ | $\Delta\gamma^d$ | $(\Delta\log E)^e$ | | (1) | (2) | (3) |
| None S-1[g] | A/B | 0.178 | — | — | 0.347 | — | — | 0.175 | 6.0 | 65.3 | 7.3 |
| Cm-1 | A | 0.136 | +0.02 | −0.08 | 0.269 | +0.66 | −0.10 | 0.359 | 1.1 | 65.5 | 1.6 |
| | B | 0.141 | −0.03 | −0.13 | 0.296 | +0.61 | −0.14 | 0.359 | 1.6 | 94.7 | 1.5 |
| B-1 | A | 0.137 | +0.03 | −0.10 | 0.275 | +0.47 | −0.11 | 0.145 | 1.1 | 65.3 | 1.6 |
| | B | 0.139 | −0.03 | −0.12 | 0.280 | +0.49 | −0.12 | 0.181 | 0.7 | 93.5 | 0.3 |
| B-2 | A | 0.164 | −0.01 | −0.05 | 0.300 | +0.11 | −0.05 | 0.150 | 7.3 | 64.2 | 5.0 |
| | B | 0.146 | −0.06 | −0.10 | 0.304 | +0.18 | −0.09 | 0.148 | 3.3 | 95.2 | 1.5 |
| B-5 | A | 0.142 | +0.13 | −0.05 | 0.302 | +0.25 | −0.05 | 0.142 | 2.4 | 4.2 | 2.4 |

[a]% Silver Remaining = $\frac{(mg/m^2 \text{ at } t = 3 \text{ min}) \times 100}{(mg/m^2 \text{ at } t = 0 \text{ min})}$

[b]The following bleach solutions or modified bleach solutions were used: (1) Bleach solution Bls1 to which 30.0 g/L of potassium bromide was added, the resulting solution diluted 1:1 with water; (2) Bleach solution Bls2: and (3) Bleach solution Bls3 diluted 7:3 with water.
[c]Interlayer (A or B), in which Barc compounds of the invention are located.
[d]Change in contrast.
[e]Speed relative to control, see footnote g.
[f]Red density measured at maximum exposure.
[g]This is the control, with 0.108 mol/m² of S-1 only, in both Interlayers A and B.

From Table 2 it can be seen that photographic elements containing compounds of the invention B-1, B-2 and B-5 have less red density at Dmax, than the comparison.

-continued
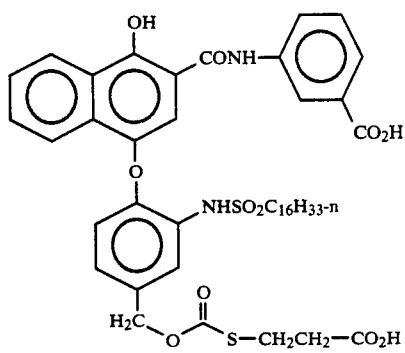
B-9
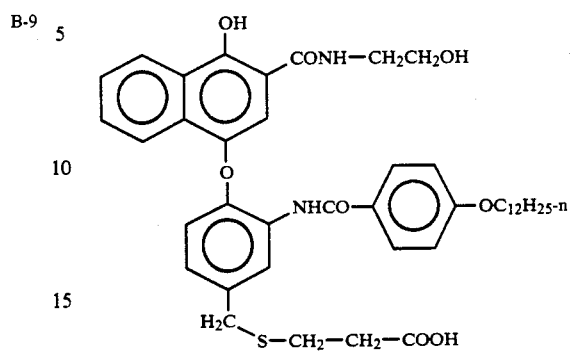
B-13
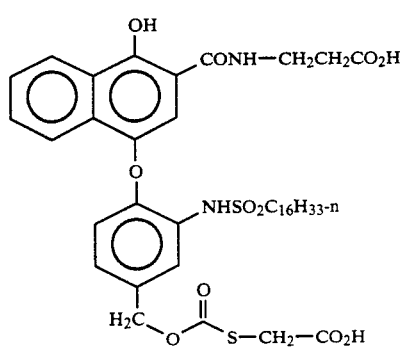
B-10
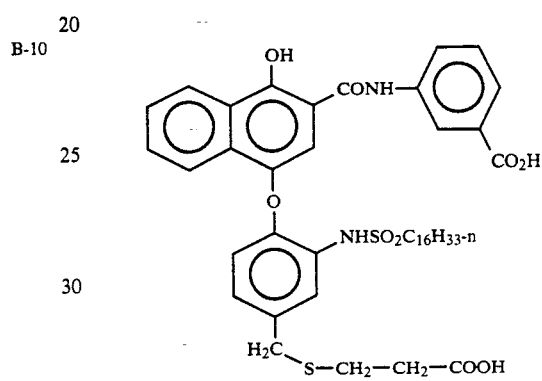
B-14
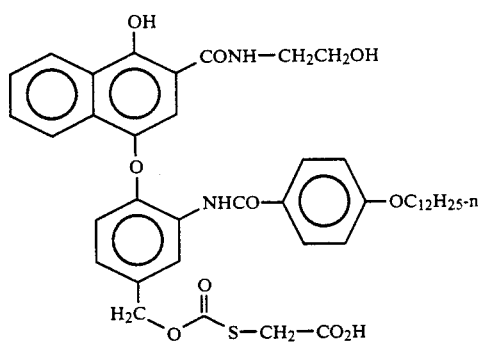
B-11
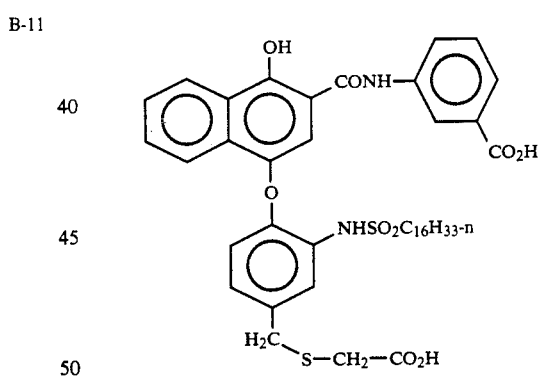
B-15
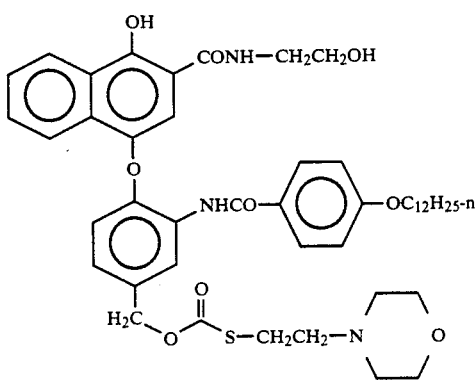
B-12
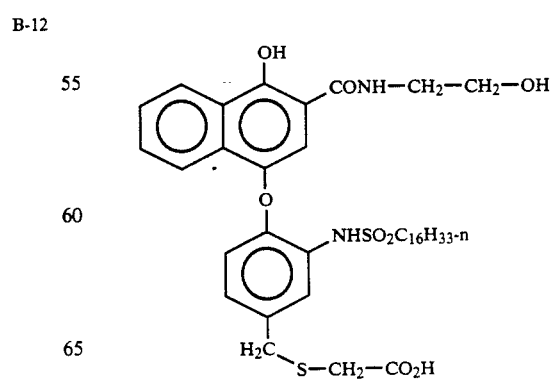
B-16

-continued
B-17
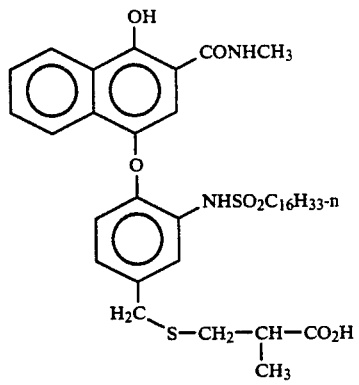
B-18
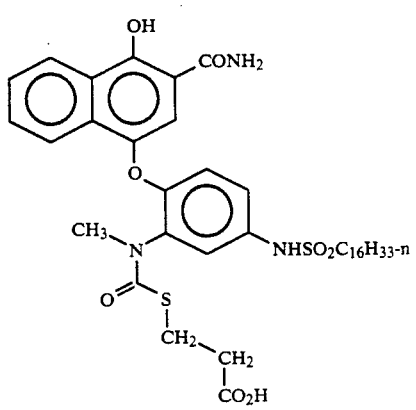
B-19
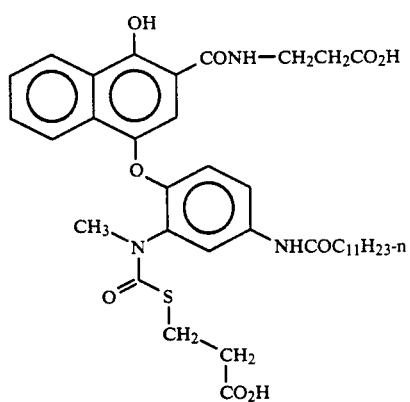
B-20
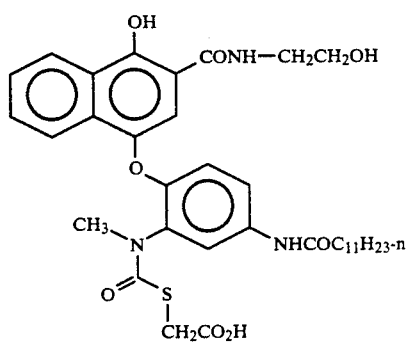
-continued
B-21
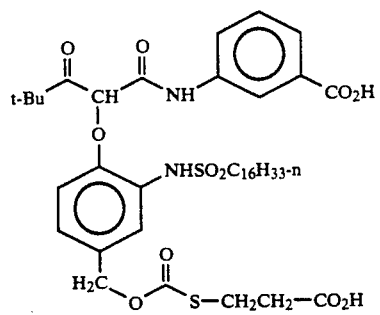
B-22
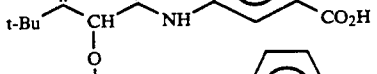
B-23
B-24
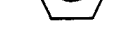
Other compounds of the invention are as follows:

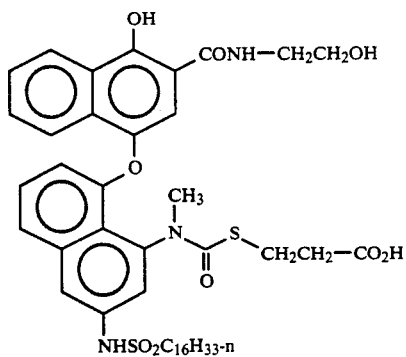
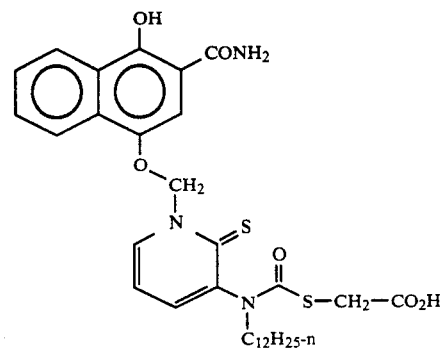
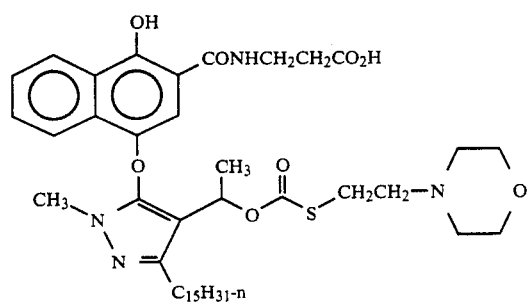
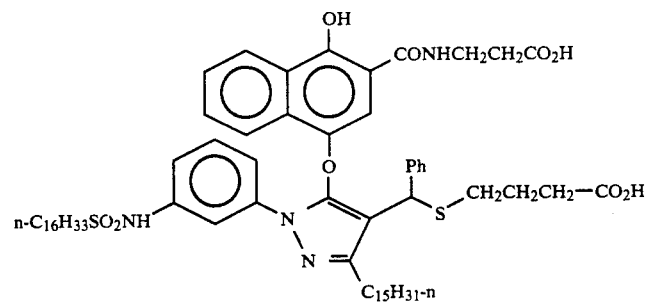
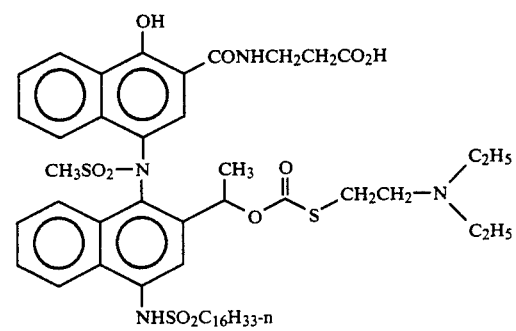

-continued
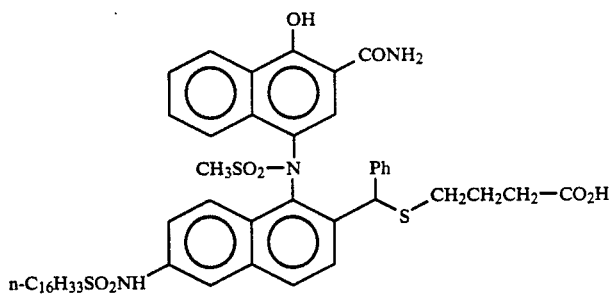
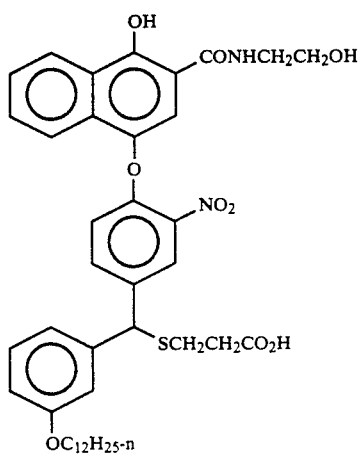
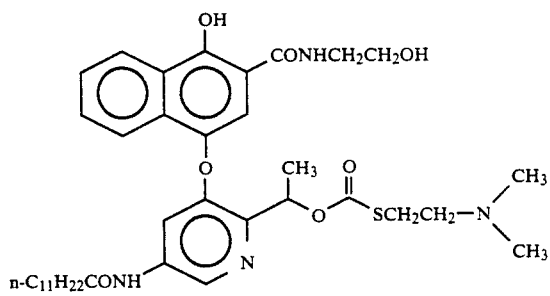
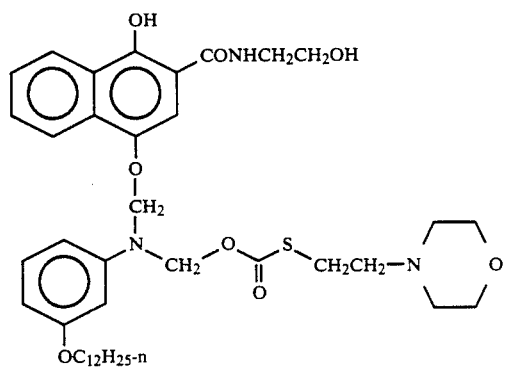

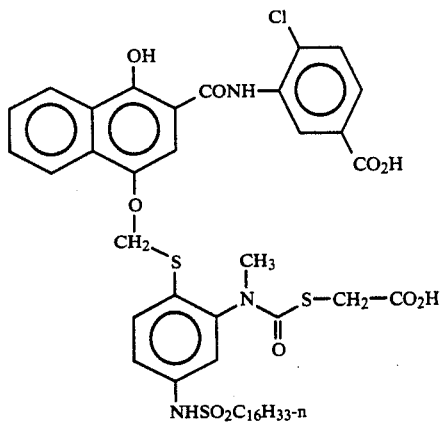

This invention has been described in detail with particular reference to preferred embodiments thereof, but it will be understood that variations and modifications can be effected within the spirit and scope of the invention.

What is claimed is:

1. A method of forming a photographic coupler selected from the group consisting of

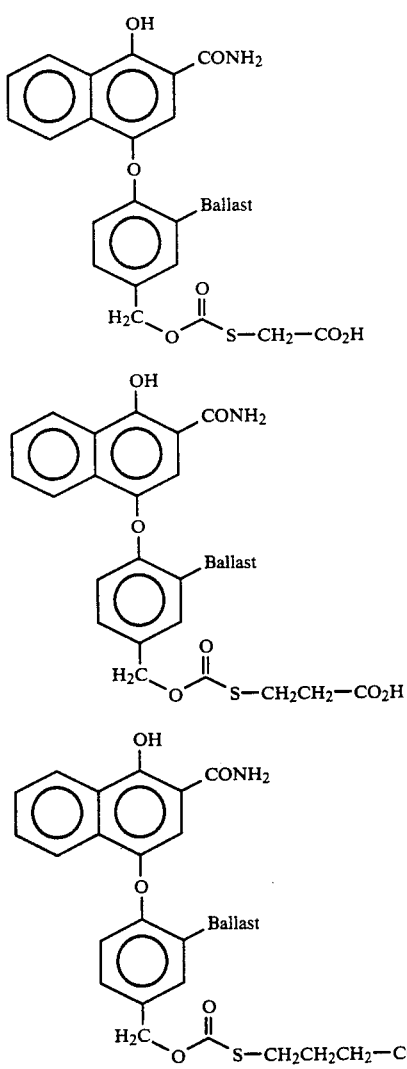

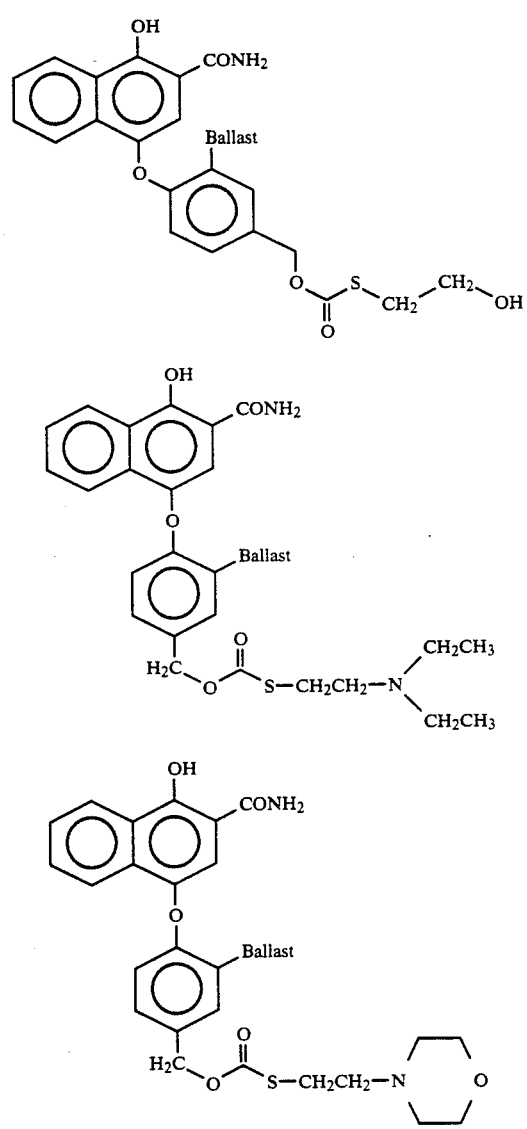

wherein:
Ballast is a photographic ballast;
the method comprising reacting phosgene with a compound having the formula

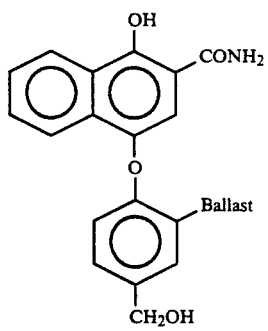

to form a chloroformate having the structure

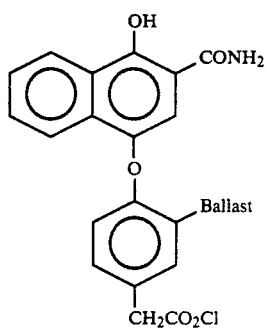

and reacting the chloroformate, in the presence of a strong base selected from the group consisting of triethylamine, N,N-diisopropylethylamine, and tetramethylguanidine, with a thiol selected from the group consisting of

HSCH$_2$COOH

HSCH$_2$CH$_2$COOH
HS(CH$_2$)$_3$COOH
HS(CH$_2$)$_2$OH

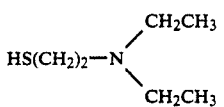

and

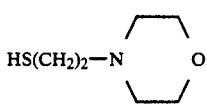

to form the photographic coupler.

2. The method according to claim 1, wherein the base is selected from triethylamine and N,N-diisopropylethylamine.

3. The method according to claim 1, wherein the photographic coupler is

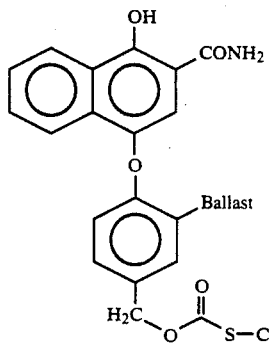

4. The method according to claim 1, wherein the photographic ballast is NHSO$_2$C$_{16}$H$_{33}$-n.

* * * * *